United States Patent [19]

Haber et al.

[11] Patent Number: 5,320,609
[45] Date of Patent: Jun. 14, 1994

[54] AUTOMATIC PHARMACEUTICAL DISPENSING SYRINGE

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 987,475

[22] Filed: Dec. 7, 1992

[51] Int. Cl.$^5$ ................................................ A61M 5/20
[52] U.S. Cl. ........................................ 604/135; 604/137
[58] Field of Search ............... 604/135, 136, 134, 137, 604/131

[56] References Cited

U.S. PATENT DOCUMENTS

| | | | |
|---|---|---|---|
| 159,192 | 1/1875 | Leiter | 604/136 |
| 1,557,836 | 10/1925 | Hein | |
| 3,659,587 | 5/1972 | Baldwin | |
| 3,696,806 | 10/1972 | Sausse | |
| 4,109,653 | 8/1978 | Kozam et al. | |
| 4,601,708 | 7/1986 | Jordon | 604/136 |
| 4,642,099 | 2/1987 | Phillips et al. | 604/136 |
| 4,717,383 | 1/1988 | Phillips et al. | 604/135 |
| 4,723,937 | 2/1988 | Sarnoff et al. | 604/136 |
| 4,738,660 | 4/1988 | Lucas | |
| 4,755,169 | 7/1988 | Sarnoff et al. | |
| 4,795,441 | 1/1989 | Bhatt | |
| 4,902,281 | 2/1990 | Avoy | |
| 5,041,088 | 8/1991 | Ritson et al. | 604/135 |
| 5,067,948 | 11/1991 | Haber et al. | |
| 5,078,691 | 1/1992 | Hamacher | |
| 5,085,641 | 2/1992 | Sarnoff et al. | 604/135 |
| 5,092,842 | 3/1992 | Bechtold et al. | 604/135 |
| 5,102,393 | 4/1992 | Sarnoff et al. | 604/135 |
| 5,114,406 | 5/1992 | Gabriel et al. | 604/136 |
| 5,176,645 | 1/1993 | Guerrero | 604/143 |

OTHER PUBLICATIONS

Novo Nordisk Magazine, pp. 2-19, Jun. 19, 1991.

*Primary Examiner*—Paul J. Hirsch
*Attorney, Agent, or Firm*—Townsend & Townsend Khourie & Crew

[57] ABSTRACT

An automatic pharmaceutical dispensing syringe (2), includes a main barrel (4) having hollow interior (18) sized to house a conventional pharmaceutical cartridge (16) and needle (6). A cap (6) at one end (8) of the main barrel is used to rotate a threaded dosing screw (158) housed within the main barrel. The dosing screw is permitted to move axially within the main barrel. The dosing screw threads (156) engage similar threads (146) on an elongate piston driver (140) which abuts the cartridge piston (152). A brake pad (194) secures the piston driver to the main barrel while the cap is rotated to select the desired dose. Doing so causes the dosing screw to move axially relative to the piston driver to compress an injection spring (174). The injection sequence is begun by placing the distal end (114) of an outer sleeve (10) surrounding the main barrel against the patient and pressing a trigger (130). This permits a needle insertion spring (106), captured between the main barrel and the outer sleeve, to drive the main barrel, cartridge and needle assembly distally, thus driving the needle into the patient. Only at the end of travel does the brake pad release the piston driver to permit the injection spring to drive the piston driver against the piston thus forcing the pharmaceutical through the needle and into the patient.

34 Claims, 14 Drawing Sheets

AUTOMATIC PHARMACEUTICAL DISPENSING SYRINGE

CROSS REFERENCE TO RELATED APPLICATIONS

This application relates to U.S. patent application Ser. No. 07/893,417 filed Jun. 1, 1992 for Dose Setting and Repeating Syringe and U.S. patent application Ser. No. 07/949,265 filed Sep. 22, 1992 for Multiple Pharmaceutical Syringe, the disclosures of which are incorporated by reference.

BACKGROUND OF THE INVENTION

Patients often need to use drug self-delivery systems which are operated by the user for routine medication injections during in-home use. Diabetics must often rely on insulin delivery systems which can be used at home or at work to administer necessary insulin. Persons undergoing human growth hormone therapy must also undergo daily injections. These self-delivery systems must be safe, accurate in dose measurement, and easy to use. Conventional syringe devices have been used in the past but place the burden of accuracy for the dose measurement upon the user.

Every diabetic patient is different and may require direct and continued medical supervision. The patient, however, is commonly instructed by the physician as to the strength, type, amount and times at which insulin must be injected on a self-injection basis. The accuracy of the dose of insulin, therefore, is extremely important. Hypoglycemia, commonly referred to as insulin reaction, can occur when the blood glucose level falls very low. Such an event can happen if a diabetic patient delays or misses a meal, exercises at a higher level or for a longer duration than usual without eating, or takes too much insulin.

In contrast, not enough insulin may result in diabetic ketoacidosis. Such a condition can create loss of appetite, thirst, drowsiness, illness or infection. In severe cases, a diabetic coma can result.

Obviously, the failure to administer accurate doses of insulin can be extreme. Therefore, diabetic patients can benefit from a reliable and accurate dose setting syringe which provides selected dose amounts to furnish accurate doses of insulin or other medication.

Human growth hormone medications are very expensive and are also very critical as to dose. When the person administering the human growth hormone is not medically trained, the use of conventional syringes can make obtaining accurate, consistent injections difficult at best.

In addition to the problems associated with accurate dosing, the process of sticking a needle into one's own or somebody else's arm or leg and expulsing the liquid pharmaceutical can be, especially for the medically untrained, quite difficult.

SUMMARY OF THE INVENTION

The present invention is directed to an automatic pharmaceutical dispensing syringe which allows the user to accurately select the desired dose by simply rotating the cap and then give the injection by simply removing the safety cap, placing the distal end of the syringe against the patient's body and then pressing a trigger on the syringe. This causes the needle to be automatically driven the correct distance into the user and, after the needle is fully inserted, the preselected dose to be automatically driven through the needle and into the patient. In this way the user is provided with an accurate dose, safely administered by one with little or no medical training.

The automatic pharmaceutical dispensing syringe is used with a cartridge of the type having a piston within a cartridge barrel, the cartridge barrel having an open proximal end and a distal end to which a needle assembly is mountable. The syringe includes a main barrel having a hollow interior sized to house the cartridge, typically with the tip of the needle extending past the distal end of the main barrel. A cap assembly is rotatably mounted to the proximal end of the main barrel and is used to rotate a threaded dosing screw housed within the main barrel. The threaded dosing screw rotates with the cap assembly and is permitted to move axially relative to the main barrel. In the preferred embodiment the cap assembly does not move axially relative to the main barrel.

The dosing screw threads engage similar threads on an elongate piston driver, also housed within the main barrel. The piston driver has a distal end which abuts the piston within the cartridge. The piston driver is keyed to the main barrel so that it cannot rotate relative to the main barrel but can move axially within the main barrel.

A brake pad is used to frictionally secure the piston driver to the main barrel when the cap assembly is rotated to select the desired dose. Doing so causes the dosing screw to move axially relative to the piston driver since the piston driver is prevented from rotating within or moving axially relative to the main barrel. The axial movement of the dosing screw compresses a pharmaceutical injection spring captured between the dosing screw and the cap assembly. Release of the brake pad permits the piston driver and dosing screw therewith to be driven against the piston of the cartridge due to the force of the pharmaceutical injection spring, thus delivering the desired dose through the needle.

The brake pad is preferably mounted within a window formed in the main barrel. The brake pad, in this preferred embodiment, applies its frictional braking force to the piston driver when an outer sleeve, mounted over the main barrel, is moved from a use position, at which a window in the outer sleeve overlies the window in the main barrel thus releasing the brake pad from its frictional engagement with the piston driver, to a safe position, at which the outer sleeve presses the brake pad inwardly against the outer, textured surface of the piston driver thus frictionally locking the piston driver in place relative to the main barrel.

A needle insertion spring is captured between the main barrel and the outer sleeve and biases the main barrel, together with the cartridge and needle assembly, in the distal direction relative to the outer sleeve. The outer sleeve is temporarily secured in the safe position by engagement of, for example, an outwardly biased latch, carried by the main barrel, with an opening formed in the outer sleeve. When in the safe position the needle is housed entirely within the outer sleeve, with the tip of the needle adjacent the distal end of the outer sleeve.

Pressing on the latch releases the latch from the opening in the outer sleeve which permits the needle insertion spring to drive the main barrel, cartridge and needle assembly distally, thus driving the needle into the patient. At the end of the travel from the safe position to the use position, the window in the outer sleeve overlies the window in the main barrel housing the brake pad thus permitting the brake pad to release the piston driver. The compressed pharmaceutical injection spring drives the piston driver against the piston thus forcing the chosen dose through the needle assembly and into the patient.

One of the primary advantages of the invention is that it permits an unsophisticated user to accurately select a desired dose and then make the injection by simply pressing a latch. The invention is compact and uses conventional or stock pharmaceutical cartridges and needle assemblies and is thus quite adaptable to a wide range of pharmaceuticals.

Other features and advantages of the invention will appear from the following description in which the preferred embodiment has been set forth in detail in conjunction with the accompanying drawings.

DESCRIPTION OF THE PREFERRED EMBODIMENT

Figure 1:
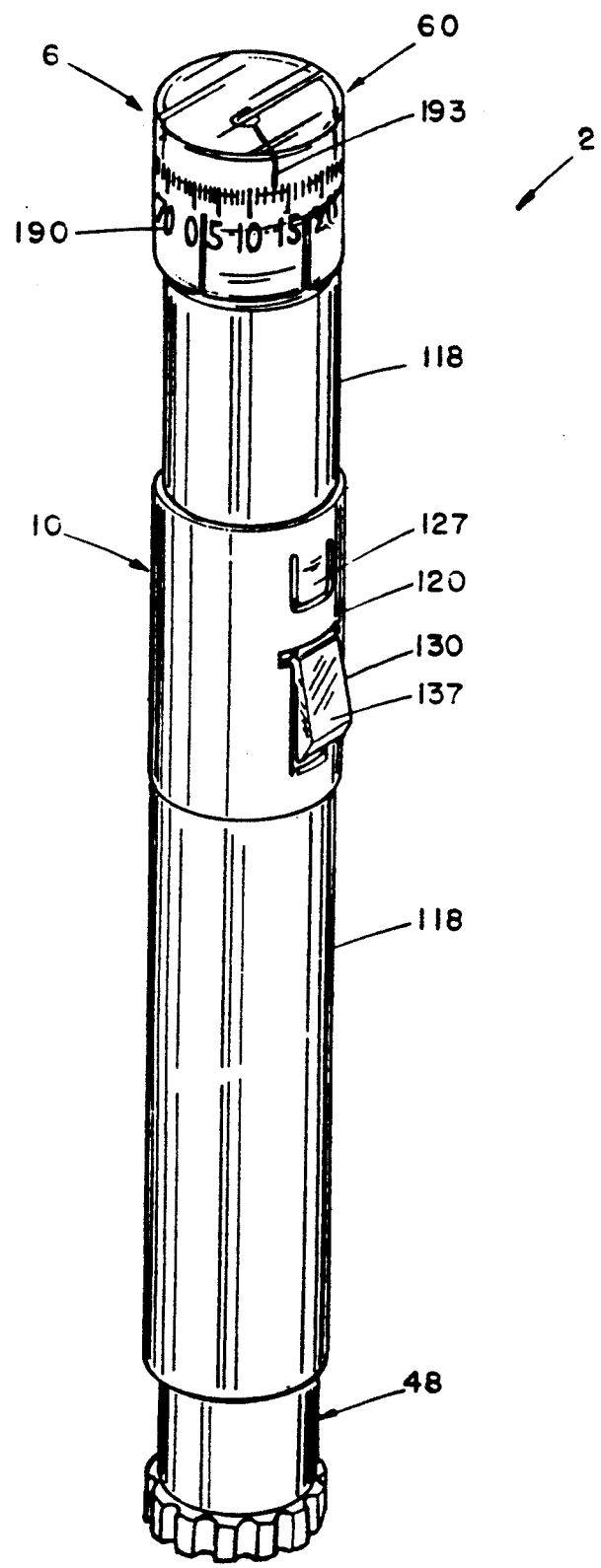
FIG. 1 is an overall perspective view of an automatic pharmaceutical dispensing syringe made according to the invention.

The figures illustrate an automatic pharmaceutical dispensing syringe 2 made according to the invention having a main barrel 4 with a cap assembly 6 mounted to a proximal end 8 of barrel 4 and surrounded by an outer sleeve 10. Main barrel 4 includes a distal end 12 having internal threads 14 formed therein. A conventional pharmaceutical cartridge 16 is housed within the distal interior region 18 of main barrel 4. Cartridge 16 is secured in place by the abutment of the open proximal end 20 of cartridge 16 with an internal ledge 22 formed within the interior of main barrel 4 at one end and a cartridge retaining nut 24 at the other. Nut 24 has external threads 26 which engage internal threads 14 at distal end 12 of main barrel 4. A proximal end 28 of nut 24 presses against the needle end 30 of cartridge 16 so that the cartridge is captured between nut 24 and ledge 22.

Nut 24 has a central bore 32 with internal threads 34 configured for mating engagement with tabs 36 formed on a needle assembly 38. Needle assembly 38 is preferably a conventional needle assembly with conventional twist lock type tabs 36. Needle assembly 38 has a needle cannula 40 extending from one end and an enlarged bore 42 sized to fit over the end of an adapter 44 at the other end. Adapter 42 is mounted to and extends from needle end 30 of cartridge 16. Distal tip 46 of needle cannula 40 extends past distal end 12 of main barrel 4 and past cartridge retaining nut 24 as well. Tip 46 would be exposed with syringe 2 in the position of FIG. 2A except for the use of a safety cap 48.

Safety cap 48 has a hollow interior 50 which houses a distal portion 51 of needle cannula 40, including distal tip 46. Cap 48 has a pair of catch arms 52 with outwardly directed protrusions 54 at the tips of arms 52. Protrusions 54 are sized and positioned to engage a pair of holes 56 formed in nut 24. Arms 52 are flexible enough to permit safety cap 48 to be snapped onto and off of nut 24 to cover an exposed distal tip 46 of needle cannula 40. Safety cap 48 is also used to mount the combination of nut 24 and needle assembly 38, which can be joined together external of main barrel 4, to distal end 12 of main barrel 4.

Cap assembly 6 includes an outer, cupped-shaped top cap 60, an intermediate, cupped-shaped locking cap 62 and inner, cupped-shaped drive cap 64. Top cap 60 is secured to the upper region 68 of the external side wall 70 of locking cap 62 by an adhesive. Side wall 70 has four slots 72 formed therein. Slots 72 permit side wall 70 to dilate sufficiently to permit an inwardly extending latching tab 74 of cap 64 to snap over and engage beneath outwardly extending latching shoulder 76 formed at the proximal end 8 of main barrel 4. The distal edge 78 of top cap 60 abuts external shoulder 80 of locking cap 62 to create a space or region 82 between a proximal surface 84 of locking cap 62 and an inner surface 86 of top cap 60. Region 82 is used to house the enlarged indicator head 88 of a dosing indicator 90 as discussed in more detail below.

A screw 92 is used to secure locking cap 62 to drive cap 64. Screw 92 passes through a countersunk hole 94 formed in surface 84 of locking cap 62 and engages threaded hole 96 formed in the end surface 98 of drive cap 64. Ultimately, top cap 60, locking cap 62 and drive cap 64 all are fixed relative to one another and rotate together. Relative axial movement between cap assembly 6 and main barrel 4 is prevented in one direction by the engagement of locking tab 74 with locking shoulder 76; movement in the other direction is prevented by the engagement of a distally facing external shoulder 100 of drive cap 64 with proximal end 8 of main barrel 4.

Figure 2A:
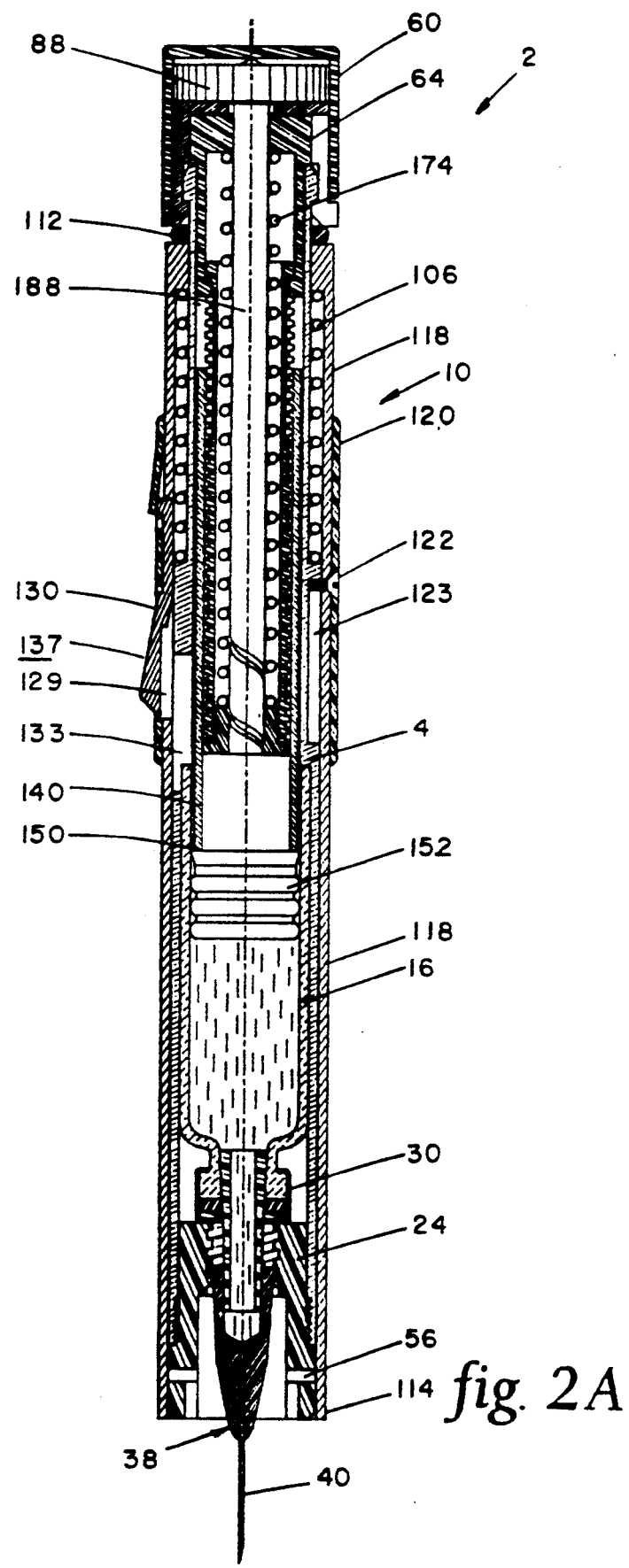
FIG. 2A is a cross-sectional view of the syringe of FIG. 1, taken through the release trigger, with the outer sleeve in the proximal or use position, the safety cap removed and after one or more injections have been made.
Figure 2B:
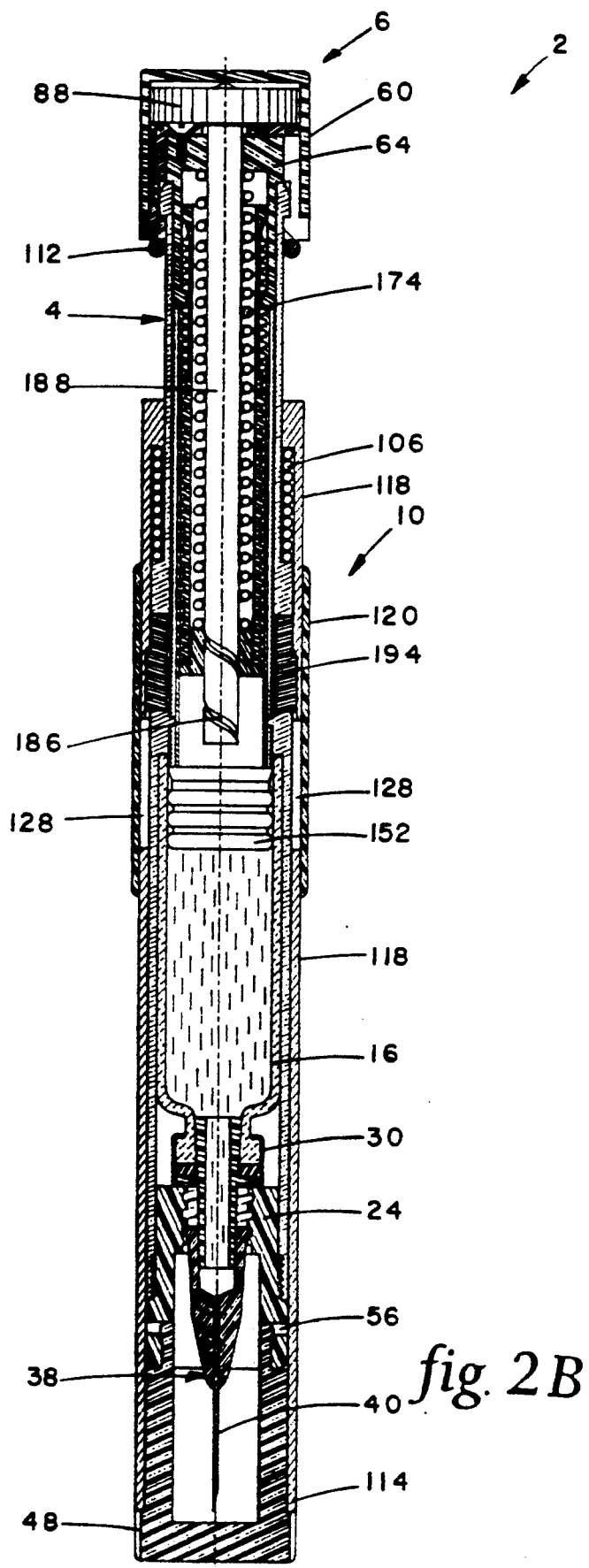
FIG. 2B is similar to FIG. 2A but prior to making any injections, with the outer sleeve in the distal or safe position and the needle insertion spring compressed, the view taken 90° from the view of FIG. 2A to illustrate the compression of the brake pads against the textured surface of the piston driver.
Figure 2C:
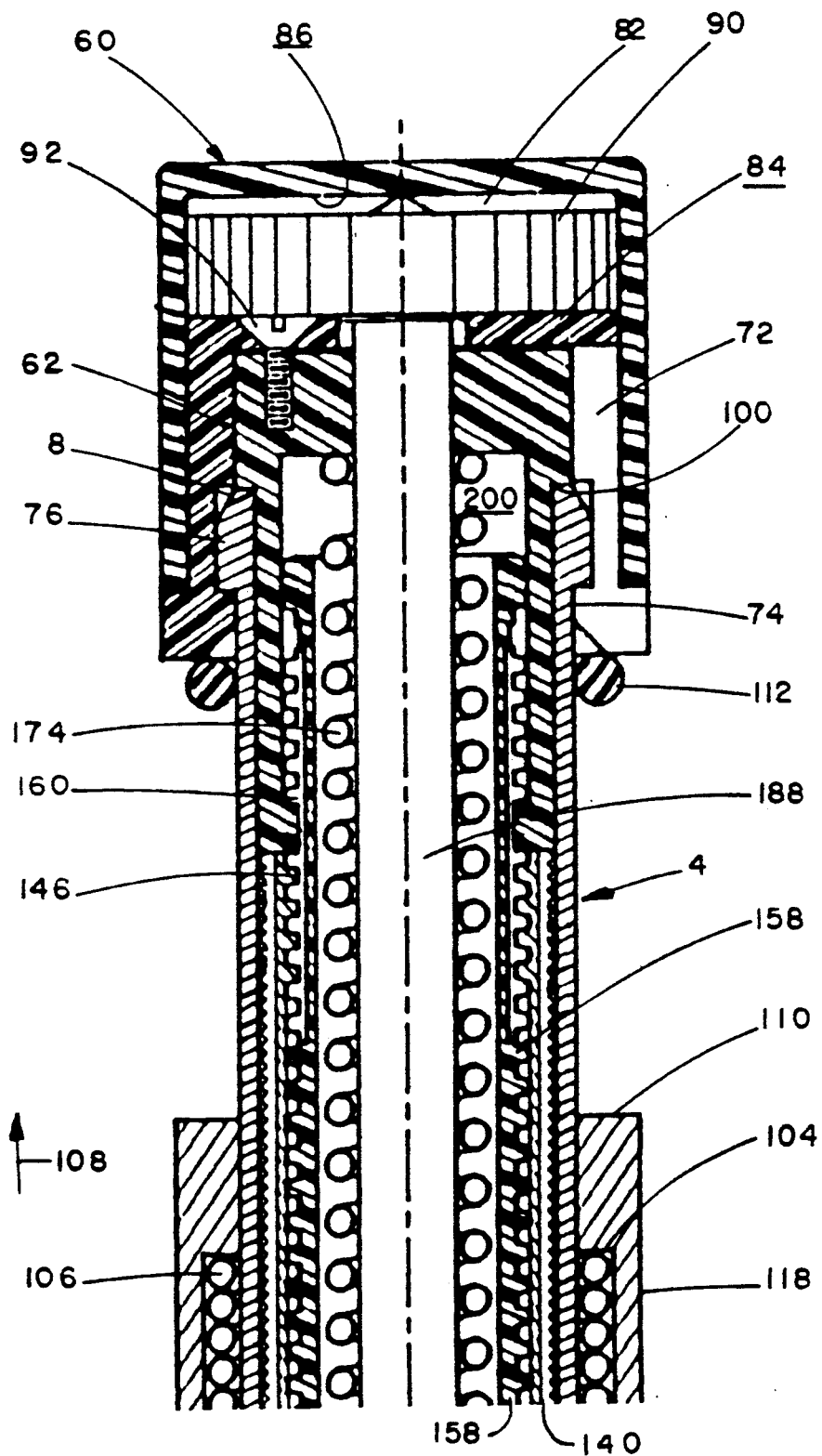
FIGS. 2C-2E are enlarged cross-sectional views of the proximal, intermediate and distal portions of the syringe of FIG. 2B.
Figure 2D:
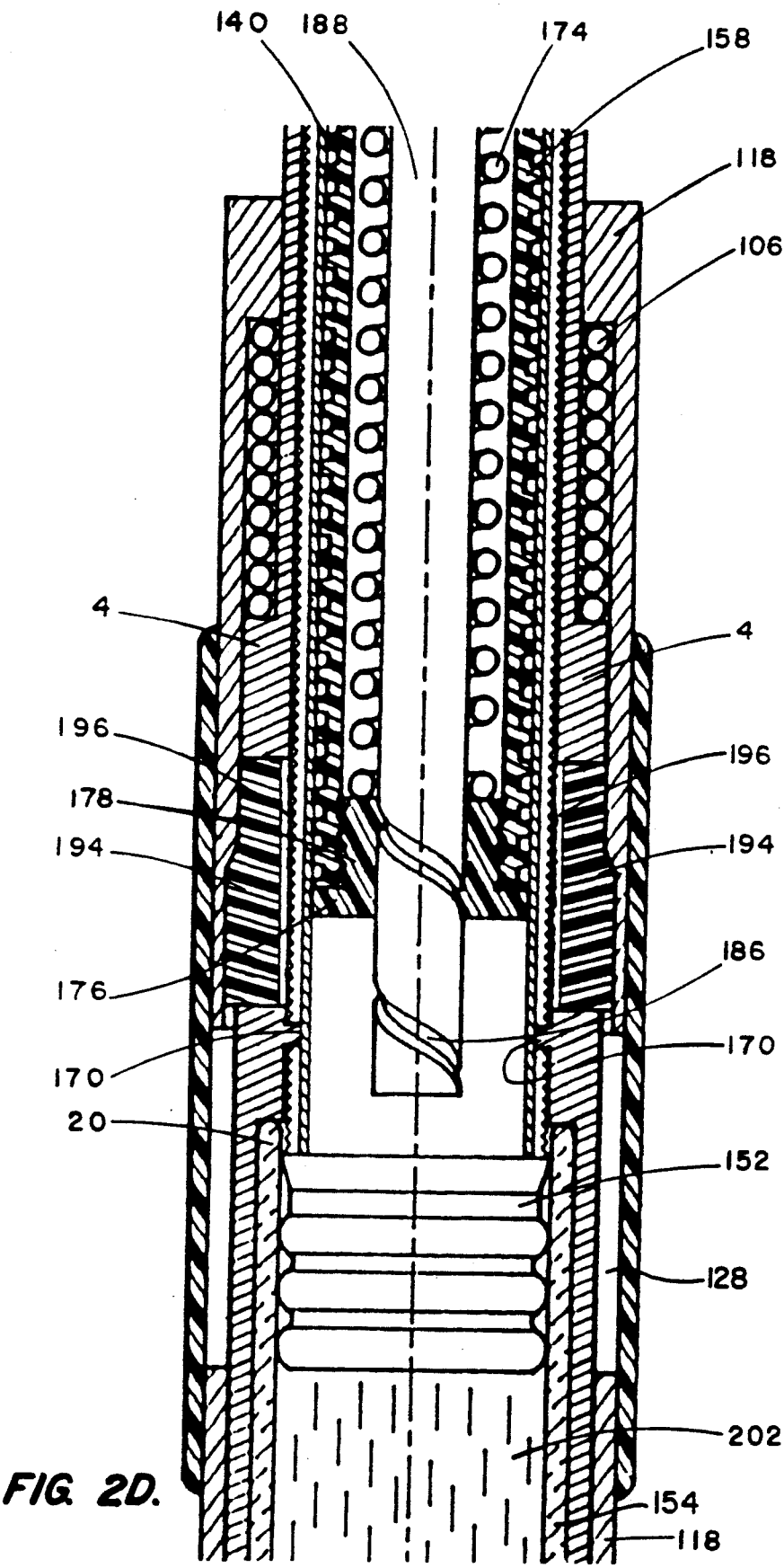
Figure 2E:
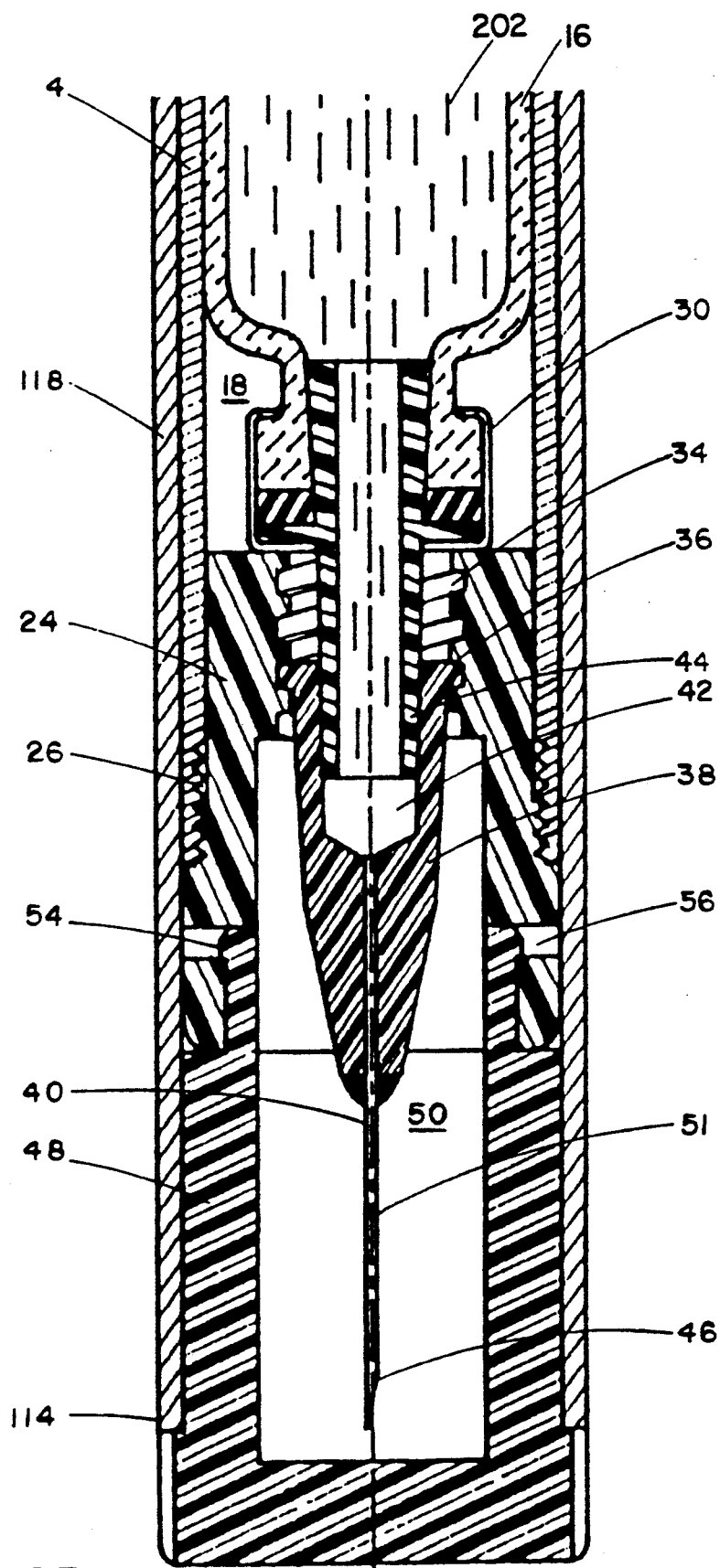

Outer sleeve 10 is movable relative to main barrel 4 between the proximal or use position of FIG. 2A and the distal or safe position of FIG. 2B. Main barrel 4 includes an external shoulder 102 facing an internal shoulder 104 of outer sleeve 10. A needle insertion spring 106 is captured between shoulders 102, 104 and biases outer sleeve 10 in the proximal direction 108, that is towards cap assembly 6. This movement is limited by the proximal end 110 of outer sleeve 10 engaging a rubber O-ring positioned adjacent locking cap 62.

Figure 3:
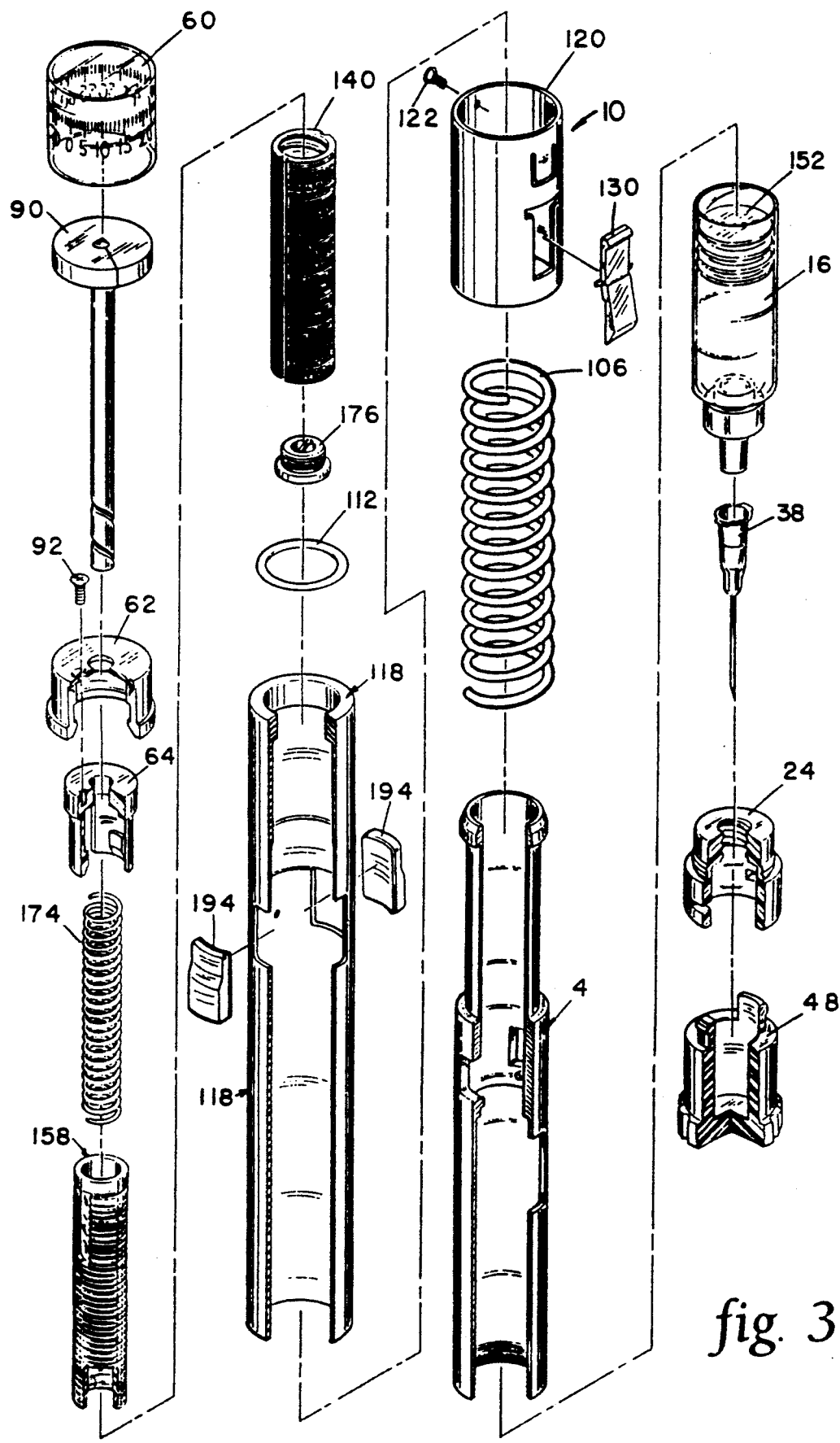
FIG. 3 is an exploded isometric view of the components constituting the syringe of FIG. 2.
Figure 3A:
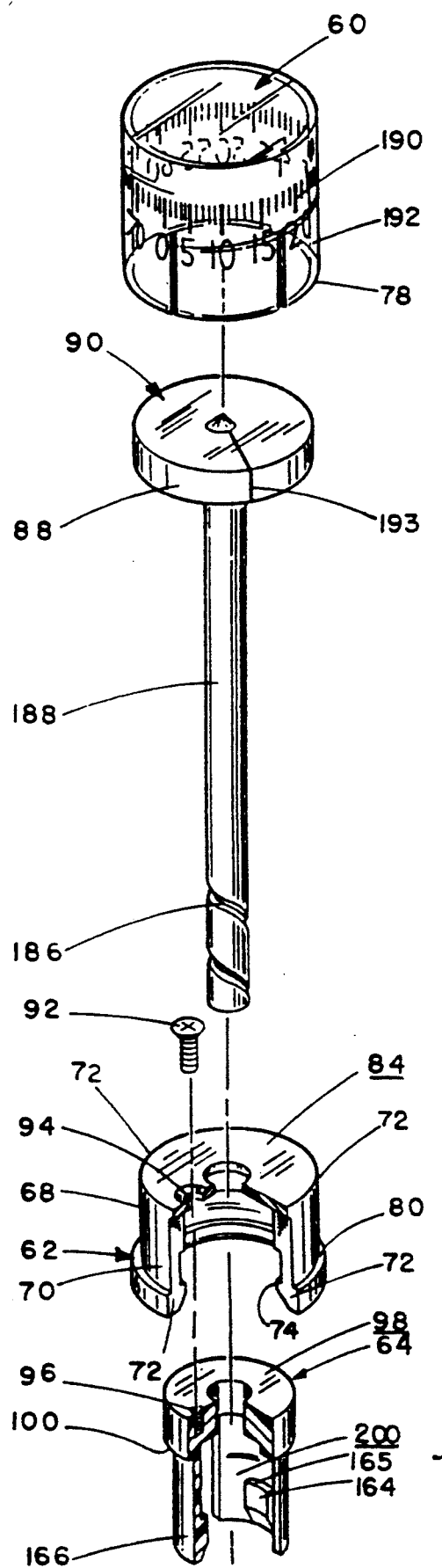
FIGS. 3A-3H are enlarged views of various groupings of the components shown in FIG. 3, with FIG. 3G being similar to FIG. 3F but rotated 180° and with a quarter section broken away.
Figure 3B:
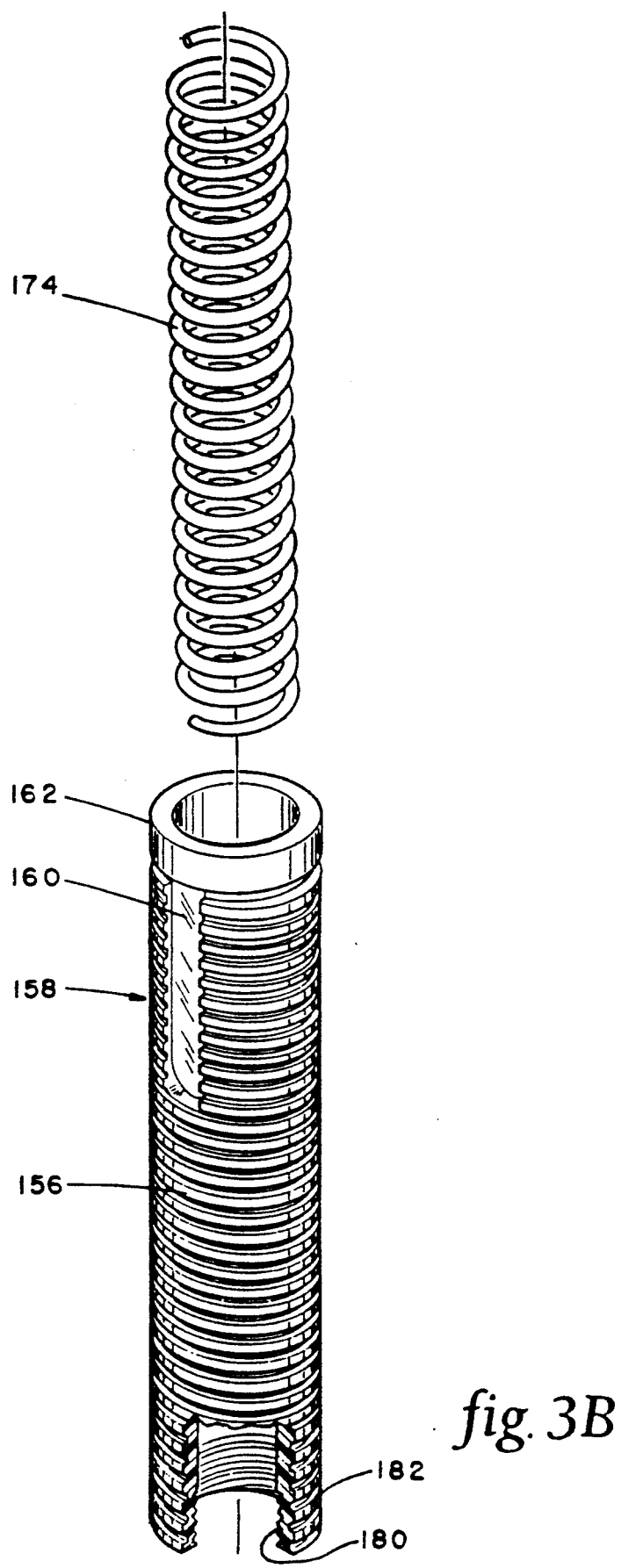
Figure 3C:
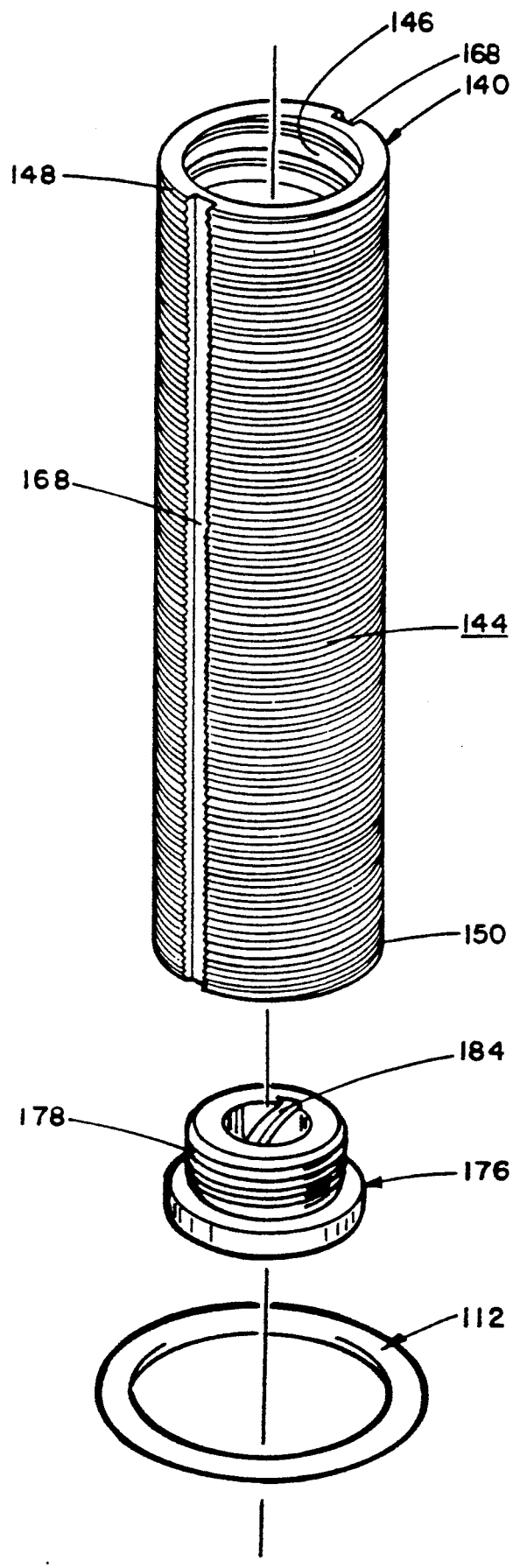
Figure 3D:
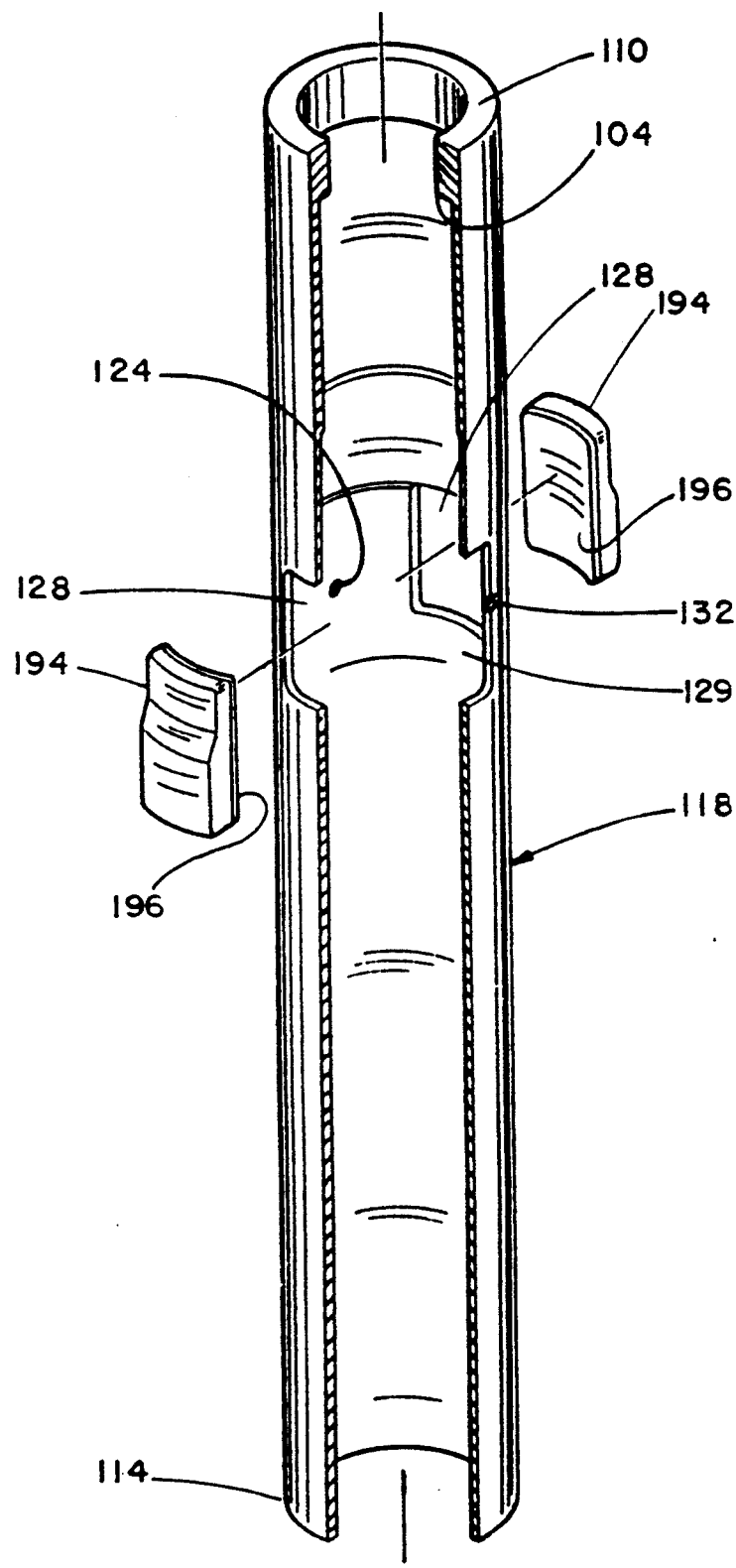
Figure 3E:
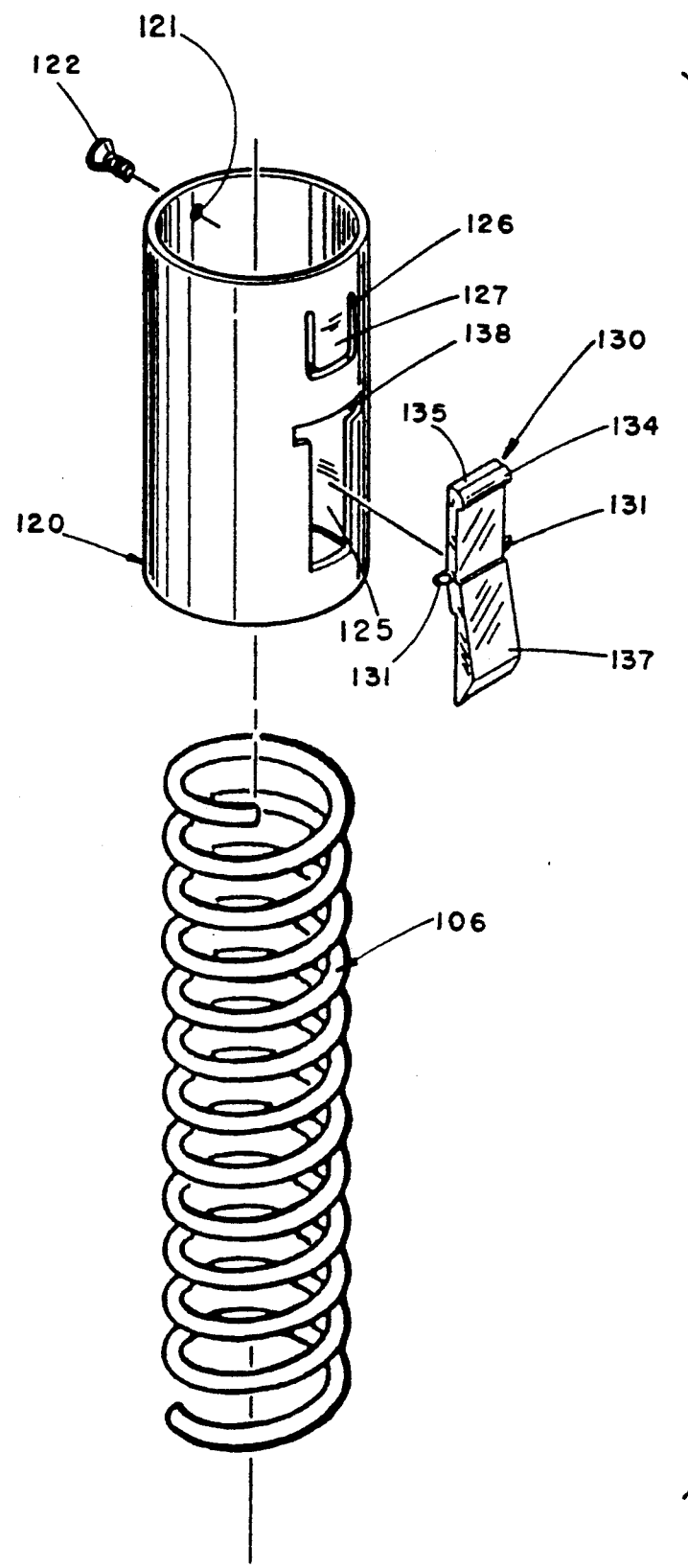
Figures 3F, 3G:
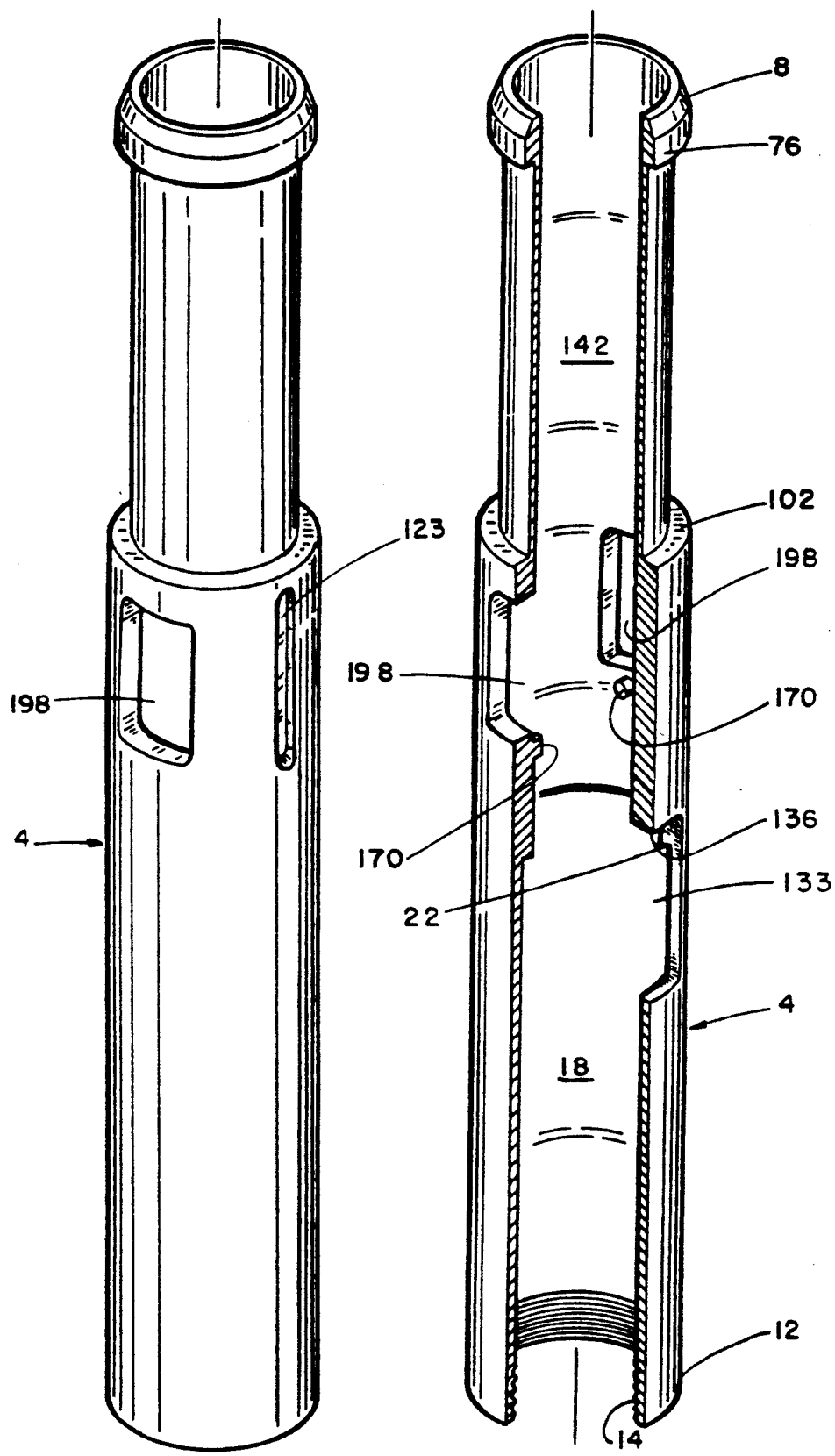
Figure 3H:
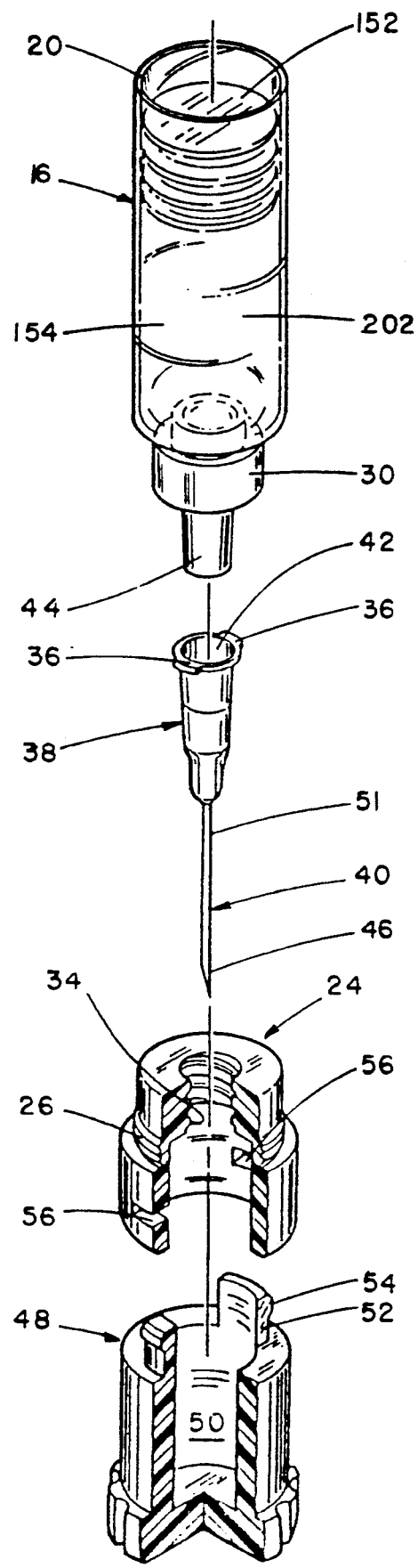

Main barrel 4 and outer sleeve 10 are about the same length. As shown in FIG. 2A, with outer sleeve 10 in the use position, the distal end 114 of sleeve 10 lies adjacent the distal end 116 of retaining nut 24. Outer sleeve 10 includes an elongate sleeve body 118 and a lock and release sleeve 120 secured to sleeve body 118 using a mounting screw 122 passing through a through hole 121 in sleeve 120 and engaging a threaded hole 124 formed in outer sleeve 10. See FIG. 3E. Screw 122 is long enough so that it passes completely through threaded hole 124 and into an axial slot 123 in main barrel 4. See FIG. 3F. This engagement of screw 122 with slot 123 permits relative axial movement between main barrel 74 and outer sleeve 10 but prevents relative rotary motion between the two.

Sleeve 120 has a T-shaped trigger installation window 125 and a U-shaped spring window 126 which defines a rectangular trigger spring 127 integral with sleeve 120. Outer sleeve 10 has a pair of brake shoe windows 128 positioned on opposite sides of sleeve 10 and a rectangular trigger window 129 aligned with but oriented 90° from brake shoe windows 128. A release trigger 130 has a pair of axles 131 extending outwardly therefrom which engage a pair of axle receptacles 132 formed in sleeve body 118 adjacent trigger window 129.

Brake shoe windows 128 are positioned to overlie windows 198 formed in main barrel 4 when outer sleeve 10 is in the use position of FIG. 2A. Main barrel 4 also has a trigger window 133 axially offset from windows 198. Trigger window 133 of main barrel 4 becomes generally aligned with trigger window 129 of outer sleeve body 118 when outer sleeve 10 is in the safe position of FIG. 2B. When this occurs, trigger spring 127, which presses against a raised portion 134 of release trigger 130, pivots release trigger 130 about axles 131 until proximal end 135 of trigger 130 engages a proximal edge 136 defining trigger window 133 of main barrel 4. An outer surface 137 of release trigger 130 passes through trigger window 129 and trigger installation window 125 so to be accessible by the user.

Trigger installation window 125 serves both to permit user access to outer surface 137 of release trigger 130 and also to install release trigger 130 into trigger window 129. That is, with outer sleeve 10 mounted over main barrel 4, enlarged end 138 of trigger installation window 125 is aligned with axle receptacles 132. Release trigger 130 is then inserted through window 125 and into window 129 so that axles 131 are positioned within axle receptacles 132. Sleeve 120 is then moved proximally until the holes 124, 121 in sleeve body 118 and sleeve 120 align so to permit screw 122 to secure the sleeve body 118 and sleeve 120 together while capturing axles 131 of trigger 130 in receptacles 132.

A cylindrical piston driver 140 is housed within the proximal interior region 142 of main barrel 4. Piston driver 140 has a textured, grooved outer surface 144 and several internal threads 146 formed at a proximal end 148 of piston driver 140. Distal end 150 of piston driver 140 abuts a piston 152 housed within cartridge barrel 154 of cartridge 16. Internal threads 146 engage the external threads 156 formed along substantially the entire length of a dose adjusting screw 158.

The dose adjusting screw has a pair of axially extending slots 160 formed towards its proximal end 162. Slots 160 are sized and positioned to be engaged by a pair of internally extending drive lugs 164 formed at the distal end 166 of drive cap 64. Rotation of cap assembly 6 causes dose adjusting screw 158 to rotate due to the engagement of drive lugs 164 within slots 160. Proximal end 162 is sized to act as a rotational stop relative to piston driver 140 by engaging threads 146 and as a translational stop relative to drive cap 64 by engaging shoulders 165 of drive lugs 164.

Piston driver 140 includes a pair of axially extending slots 168 formed in textured surface 144. Main barrel 4 includes a pair of radially inwardly extending pins 170 positioned to engage slots 168 to permit piston driver 140 to move axially within main barrel 4 but not rotate within main barrel 4. Because of this, rotation of cap assembly 6, which cause similar rotation of dose adjusting screw 158, will require telescoping of, that is relative axial movement between, dose adjusting screw 158 and piston driver 140.

The free movement of piston driver 140 in distal direction 172 is resisted by the contact of distal end 150 with piston 152. Free movement of dose adjustment screw 158 in proximal direction 108 is resisted by a pharmaceutical injection spring 174. Spring 174 is captured between an indicator drive nut 176 at one end and drive cap 64 at the other.

Nut 176 has external threads 178 which engage mating internal threads 180 formed at the distal end 182 of dose adjusting screw 158. Nut 176 is secured onto distal end 182 of dose adjusting screw 158 with sufficient force so that nut 176 and screw 158 rotate together as a unit. Nut 176 has an internal thread 184 which engages an external dose indicator thread 186 formed along a stem 188 of dose indicator 90.

Threads 156 of dose adjusting screw 158 and indicator thread 186 have greatly differing pitches. Preferably the pitch of thread 186 is at least two times and is preferably four times the pitch of thread 156. Thus, rotating cap assembly 6 one revolution will cause dosing indicator 90, through the engagement of nut 176 with stem 188, to rotate one-quarter turn. This difference in rotation can be observed by viewing enlarged indicator head 188 through clear top cap 60. Top cap 60 has dose indicia 190 formed around its circumferential side wall 192 while head 188 has a dose indicator line 193 formed thereon to align with indicia 190. Indicia 190 are preferably in units of medication. In the preferred embodiment the maximum dose obtainable, 70 units, is achieved by rotating cap assembly 6 four complete revolutions. With a four to one ratio, the actual dose to be delivered will be indicated by where dose indicator line 193 lies relative to dose indicia 190.

If one were to rotate the cap assembly 6 in the use condition of FIG. 2A, the relative axial movement between dose adjusting screw 158 and piston driver 140 would cause either compression of spring 174 or movement of piston 152, or both, depending upon the compression force of spring 174 and the resistance to movement of piston 152. However, to prevent this from occurring, a pair of brake pads 194 are used. Brake pads 194 are typically made of a hard plastic, such as polycarbonate, and have a curved inner surface 196 made of a resilient, high friction material, such as latex or butyl rubber. Pads 194 are housed within windows 198 formed in main barrel 4. Outer sleeve 10, when in the distal or safe position of FIG. 2B, presses brake pads 194 against textured surface 144 of piston driver 140 to create a high friction interface between the two. Thus, when outer sleeve 10 is in the distal or safe position, piston driver 140 is prevented from moving axially within main body 4. Accordingly, rotation of cap assembly 6 in this situation causes dose adjusting screw 158 to move in proximal direction 108 with the proximal end 162 of screw 158 moving into the interior 200 of drive cap 64.

The use of syringe 2 proceeds generally as follows. A full cartridge 16 is placed in region 18 of main barrel 4 and retained in placed by cartridge retaining nut 24. A needle assembly 38 is mounted to cartridge retaining nut 24 and safety cap 48 is mounted to nut 24 to cover the exposed distal portion 51 of needle cannula 40. The outer sleeve 10 is moved distally until the release trigger 130 engages main barrel 4 at edge 136 and secures outer sleeve 10 in the safe position of FIG. 2B. The desired dose is chosen by rotating cap assembly 6 until dose indicator line is aligned with the appropriate dose indicium along dose indicia 190.

The user then removes safety cap 48 from cartridge retaining nut 24 and places distal end 114 of outer sleeve 10 against the person to receive the injection. The user then holds syringe 2 by grasping outer sleeve 10 and presses on outer surface 137 of release trigger 130 thus moving end 135 of trigger 130 away from edge 136 of main barrel 4. This permits spring 106 to drive everything except for outer sleeve 10 and the proximal end of needle insertion spring 106 in distal direction 172 thus driving distal tip 46 into the patient. This movement ceases when proximal end 110 of outer sleeve 10 contacts O-ring 12. At the end of this movement, windows 128 are aligned with windows 198 thus releasing surfaces 196 of brake pads 194 from textured surface 144 of piston driver 140. This permits spring 174 to drive dose adjusting screw 158 and piston driver 140 therewith in distal direction 172 thus causing the piston driver to drive piston 152 further into the interior of cartridge 16 forcing the liquid pharmaceutical 202 within cartridge 16 through needle cannula 40 and into the patient. The axial movement of indicator drive nut 166 in distal direction 172 causes dose indicator 90 to rotate back to an initial or starting position, typically with dose indicator line 193 aligned with a zero value along dose indicia 190. Safety cap 48 is then resecured to nut 24 to cover needle cannula 40.

Cartridge 16 and needle assembly 38 are generally conventional in construction, such as made by Eli Lilly Co. of Indianapolis, Ind. for use with reconstituted synthetic growth hormone. Other conventional or nonconventional cartridges and needle assemblies could be used as well. Springs 174, 106 and piston driver 140 are made of stainless steel. Main barrel 4 is made of a self-lubricating plastic, such as an acetyl resin sold by DuPont Co. of Wilmington, Del. under the trademark DELRIN. Outer sleeve 10 is preferably aluminum for aesthetic reasons and for strength. The remaining components not already discussed can be made of polycarbonate. Other materials can be used for the various components.

Modification and variation can be made to the disclosed embodiment without departing from the subject of the invention as defined in the following claims. For example, springs 106, 174 could be replaced by pneumatic springs. The display readout could be electronic instead of mechanical. Most of the components could be made of clear materials to permit the user to see the expulsion of liquid pharmaceutical 202. Other types of cartridges could be used, such as the type having a pierceable septum at one end which is accessed by a double ended needle. The cartridge could be replaced by other variable-volume pharmaceutical containers, such as collapsible bags or bellows arrangements. The braking mechanism could be replaced by electrical or hydraulic brakes which respond to the position of outer sleeve 10 relative to main body 4.

What is claimed is:

1. A pharmaceutical dispensing syringe, for use with a needle assembly and a cartridge of the type having a cartridge barrel, an open end, a needle end to which the needle assembly is mountable, a piston within the barrel and a flowable pharmaceutical within the barrel between the piston and the needle end, the needle assembly having a tip, the syringe comprising:

a main barrel having a proximal end, a distal end and a hollow interior sized to house the cartridge therein, the tip of the needle assembly extending past the distal end;

a user manipulatable cap rotationally mounted to the proximal end of the barrel;

a dosing screw, including dosing screw threads, rotationally driven by the cap whereby rotation of the cap allows the user to select a dose of the pharmaceutical to be dispensed through the needle assembly;

a piston driver threadably coupled to the dosing screw and having a distal driver end engaging the piston;

a dosing spring captured between the cap and dosing screw, the dosing spring biasing the piston driver against the piston;

a user actuated brake device selectively securing the piston driver to the main barrel to prevent relative axial movement therebetween until released by the user;

an outer sleeve slidably mounted over the main barrel and movable between a safe position, with the outer sleeve enclosing the needle assembly, and a use position, with the tip of the needle assembly exposed;

an injection spring captured between the main barrel and the outer sleeve biasing the main barrel, cartridge and needle assembly in a distal direction relative to the outer sleeve; and a release trigger mounted within an opening in the outer sleeve, the trigger, when the outer sleeve is in the safe position, preventing the injection spring from driving the main barrel, cartridge and needle assembly in a distal direction until released by the user.

2. The syringe of claim 1 wherein:

the dosing screw threads are external threads;

the piston driver is hollow and has internal threads which mate with the external threads of the dosing screw; and the dosing screw is coupled to the cap using a radially extending drive element on the cap which engages an axially extending groove formed in the dosing screw.

3. The syringe of claim 1 wherein the brake device includes a brake pad housed within a window formed in the main barrel, the brake pad movable between a brake applied position and a brake released position by movement of the outer sleeve between the safe position and the use position.

4. The syringe of claim 1 further comprising a dosing indicator operably coupled to the dosing screw.

5. The syringe of claim 4 wherein the dosing indicator includes:

a stem having a dose indicator thread;

an indicator head secured to the stem; and a dose indicator drive nut secured to the dosing screw and threadably engaging the dose indicator thread so that rotating the cap causes relative rotary motion between the cap and the indicator head.

6. The syringe of claim 5 wherein the cap includes a top cap including a transparent region and a hollow interior, the indicator head being housed within the hollow interior.

7. The syringe of claim 6 wherein one of the top cap and the indicator head includes dose indicia and the other of the top cap and the indicator head includes a dose indicator marker positioned to align with the dose indicia according to the dose to be dispensed.

8. The syringe of claim 6 wherein the indicator head is disc-shaped.

9. The syringe of claim 5 wherein the pitch of the indicator thread is at least two times the pitch of the dosing screw threads so that the relative rotary motion between the cap and the main barrel is at least two times the relative rotary motion between the cap and the indicator head.

10. The syringe of claim 3 wherein the outer sleeve encloses the needle assembly when the outer sleeve is in the brake applied position, and the tip of the needle assembly is exposed when the outer sleeve is in the brake released position.

11. The syringe of claim 10 wherein the injection spring, when released by the release trigger, drives the main barrel, cartridge and needle assembly therewith within the outer sleeve from the brake applied position of the outer sleeve to the brake released position of the outer sleeve permitting the tip of the needle assembly to be driven into the patient during said movement and substantially releasing the piston driver from the main barrel at the end of said movement to permit the dosing spring to drive the piston driver toward the piston according to the rotary position of the cap.

12. A pharmaceutical dispensing syringe, for use with a needle assembly and a cartridge of the type having a cartridge barrel, an open end, a needle end to which the needle assembly is mountable, a piston within the barrel and a flowable pharmaceutical within the barrel between the piston and the needle end, the needle assembly having a tip, the syringe comprising:
a main barrel having a proximal end, a distal end and a hollow interior sized to house the cartridge therein, the tip of the needle assembly extending past the distal end;
a user manipulatable cap rotationally mounted to the proximal end of the barrel;
a dosing screw, including dosing screw threads, housed within the main barrel and rotationally driven by the cap, the dosing screw being coupled to the cap to permit relative axial movement therebetween;
a piston driver threadably coupled to the dosing screw threads and having a distal driver end continuously engaging the piston;
means for biasing the piston driver towards the piston; and
means for preventing the piston driver from rotating within the main barrel so that rotary motion of the cap causes rotary motion of the dosing screw which causes relative axial motion between the dosing screw and the piston driver.

13. The syringe of claim 12 wherein:
the dosing screw has external threads;
the piston driver is hollow and has internal threads which mate with the external threads of the dosing screw;
the dosing screw is coupled to the cap using a radially extending drive element on the cap which engages an axially extending groove formed in the dosing screw; and
the biasing means includes a compression coil spring captured between the cap and the dosing screw.

14. The syringe of claim 12 further comprising a user actuated brake device selectively securing the piston driver to the main barrel to prevent relative axial movement therebetween until the brake device is released by the user.

15. The syringe of claim 14 wherein the brake device includes a brake pad housed within a window formed in main barrel and a slidable outer sleeve slidably mounted over the main barrel for movement between a brake applied position, at which the brake pad frictionally secures the piston driver to the main barrel, and a brake released position, at which the brake pad substantially releases the piston driver from the main barrel.

16. The syringe of claim 12 further comprising a dosing indicator operably coupled to the dosing screw.

17. The syringe of claim 16 wherein the dosing indicator includes:
a stem having a dose indicator thread;
an indicator head secured to the stem; and
a dose indicator drive nut secured to the dosing screw and threadably engaging the dose indicator thread so that rotating the cap causes relative rotary motion between the cap and the indicator head.

18. The syringe of claim 17 wherein:
the cap includes a top cap including a transparent region and a hollow interior, the indicator head being housed within the hollow interior; and
one of the top cap and the indicator head includes dose indicia and the other of the top cap and the indicator head includes a dose indicator marker positioned to align with the dose indicia according to the dose to be dispensed.

19. The syringe of claim 12 further comprising an outer sleeve, having sleeve distal and sleeve proximal ends, slidably mounted over the main barrel and movable between a safe position, with the outer sleeve enclosing the needle assembly, and a use position, with the tip of the needle assembly exposed.

20. The syringe of claim 19 further comprising user actuated means for driving the main barrel, cartridge and needle assembly therewith within the outer sleeve from the safe position to the use position permitting the tip of the needle assembly to be driven into the patient.

21. The syringe of claim 15 wherein the outer sleeve encloses the needle assembly when the outer sleeve is in the brake applied position, and the tip of the needle assembly is exposed when the outer sleeve is in the brake applied position.

22. The syringe of claim 21 further comprising user actuated means for driving the main barrel, cartridge and needle assembly therewith within the outer sleeve from the brake applied position of the outer sleeve to the brake released position of the outer sleeve permitting the tip of the needle assembly to be driven into the patient during said movement and substantially releasing the piston driver from the main barrel at the end of said movement to permit the piston driver biasing means to drive the piston drives toward the piston according to the rotary position of the cap.

23. A pharmaceutical dispensing syringe, for use with a needle assembly and a cartridge of the type having a cartridge barrel, an open end, a needle end to which the needle assembly is mountable, a piston within the barrel and a flowable pharmaceutical within the barrel between the piston and the needle end, the needle assembly having a tip, the syringe comprising:
a main barrel having a proximal end, a distal end and a hollow interior sized to house the cartridge therein, the tip of the needle assembly extending past the distal end;

a user manipulatable cap rotationally mounted to the proximal end of the barrel;

a dosing screw, including dosing screw threads, housed within the main barrel and rotationally driven by the cap, the dosing screw being coupled to the cap to permit relative axial movement therebetween;

a piston driver threadably coupled to the dosing screw threads and having a distal driver end engaging the piston;

means for biasing the piston driver towards the piston;

means for preventing the piston driver from rotating within the main barrel so that rotary motion of the cap causes rotary motion of the dosing screw which causes relative axial motion between the dosing screw and the piston driver;

an outer sleeve slidably mounted over the main barrel movable between a safe position, at which the outer sleeve covers the tip of the needle assembly, and a use position, at which the tip of the needle is exposed;

a brake pad housed with a window formed between the main barrel and the outer sleeve for movement between a brake applied position, at which the brake pad frictionally secures the piston driver to the main barrel, and a brake released position, at which the brake pad substantially releases the piston driver from the main barrel; and a brake actuator element which keeps the brake pad in the brake applied position until the outer sleeve is at the use position.

24. The syringe of claim 23 further comprising a dosing indicator, operably coupled to the dosing screw, the dosing indicator including:

a stem having a dose indicator thread;

an indicator head secured to the stem; and a dose indicator drive nut secured to the dosing screw and threadably engaging the dose indicator thread so that rotating the cap causes relative rotary motion between the cap and the indicator head.

25. A method for automatically dispensing a desired dose of liquid pharmaceutical from a cartridge, of the type having a body with an open end, a needle end, a piston within the body and a flowable pharmaceutical within the body between the piston and the needle end, through the needle of a needle assembly fluidly coupled to the body, the method comprising the steps of:

providing a main barrel having a proximal end, a distal end and a hollow interior sized to house the cartridge therein;

sliding an outer sleeve slidably mounted over the barrel from a use position, with the needle being exposed, to a safe position, with the outer sleeve enclosing the needle, to compress an injection spring captured between the outer sleeve and the main barrel;

securing the injection spring when the outer sleeve is in the safe position;

securing a piston driver to the main barrel to prevent relative axial movement therebetween;

placing a distal end of the outer sleeve against a patient;

rotating a cap mounted to the proximal end of the barrel to compress a dosing spring;

releasing the injection spring;

driving the main barrel, cartridge and needle assembly in a distal direction so to inject the needle into a patient;

releasing the piston driver after the needle is injected into the patient; and driving the piston driver against the piston to force the desired dose of pharmaceutical within the cartridge through the needle and into the patient.

26. The method of claim 25 wherein the injection spring securing step is carried out with a trigger mounted in an opening in the outer sleeve.

27. The method of claim 25 wherein the piston driver securing step includes the step of moving a brake device housed within a window formed within the main barrel from a brake release position to a brake applied position.

28. The method of claim 25 wherein the rotating step is carried out with a dosing screw coupled to the cap so that the dosing screw moves in an axial direction when the cap is rotated, the dosing screw being threadably coupled to the piston driver, the dosing spring being captured between the cap and the dosing screw.

29. The method of claim 26 wherein the injection spring releasing step includes the step of pressing the trigger.

30. The method of claim 27 wherein the piston driver releasing step includes the step of moving the brake device from the brake applied position to the brake release position.

31. A pharmaceutical dispensing syringe, for use with a needle assembly and a cartridge of the type having a cartridge barrel, an open end, a needle end to which the needle assembly is mountable, a piston within the barrel and a flowable pharmaceutical within the barrel between the piston and the needle end, the needle assembly having a tip, the syringe comprising:

a main barrel having a proximal end, a distal end and a hollow interior sized to house the cartridge therein, the tip of the needle assembly extending past the distal end;

a piston driver having a distal driver and engagable with the piston;

means, operably coupled with the piston driver, for selecting a dose of the pharmaceutical to be dispensed through the needle assembly;

first driving means for driving the tip of the needle assembly into a patient; and second driving means, separate from the first driving means, for driving the piston driver against the piston a selected distance, corresponding to the selected dose, after the first driving means has driven the tip of the needle assembly into the patient.

32. The syringe of claim 31 wherein the selecting means includes:

a user manipulatable cap rotationally mounted to the proximal end of the barrel; and a dosing screw, including dosing screw threads, rotationally driven by the cap, the dosing screw threadably coupled to the piston driver.

33. The syringe of claim 32 wherein the first driving means includes:

a dosing spring captured between the cap and dosing screw, the dosing spring biasing the piston driver against the piston;

means for preventing the piston driver from rotating within the main barrel so that rotary motion of the cap causes rotary motion of the dosing screw which causes relative axial motion between the dosing screw and the piston driver; and a user actuated brake device selectively securing the piston driver to the main barrel to prevent relative axial motion therebetween until released by the user.

34. The syringe of claim 31 wherein the second driving means includes:

an outer sleeve slidably mounted over the main barrel and movable between a safe position, with the outer sleeve enclosing the needle assembly, and a use position, with the tip of the needle assembly exposed;

an injection spring captured between the main barrel and the outer sleeve biasing the main barrel, cartridge and needle assembly in a distal direction relative to the outer sleeve; and a release trigger mounted within an opening in the outer sleeve, the trigger, when the outer sleeve is in the safe position, preventing the injection spring from driving the main barrel, cartridge and needle assembly in a distal direction until released by the user.

* * * * *